US010808099B2

(12) United States Patent
Boutillier et al.

(10) Patent No.: US 10,808,099 B2
(45) Date of Patent: *Oct. 20, 2020

(54) POLYMERIC COMPOSITION ABSORBING, COMPRISING AND RELEASING AN ODORIFEROUS ACTIVE COMPOUND, METHOD FOR PREPARING IT AND ITS USE

(71) Applicant: Arkema France, Colombes (FR)

(72) Inventors: Jean-Marc Boutillier, Sauvagnon (FR); Arnaud Pillion, Pau (FR)

(73) Assignee: Arkema France, Colombes (FR)

( * ) Notice: Subject to any disclaimer, the term of this patent is extended or adjusted under 35 U.S.C. 154(b) by 48 days.

This patent is subject to a terminal disclaimer.

(21) Appl. No.: 15/552,042

(22) PCT Filed: Feb. 19, 2016

(86) PCT No.: PCT/EP2016/053581
§ 371 (c)(1),
(2) Date: Aug. 18, 2017

(87) PCT Pub. No.: WO2016/131969
PCT Pub. Date: Aug. 25, 2016

(65) Prior Publication Data
US 2018/0037715 A1    Feb. 8, 2018

(30) Foreign Application Priority Data
Feb. 20, 2015   (FR) ..................... 15 51473

(51) Int. Cl.
| C08K 5/00 | (2006.01) |
| A61L 9/014 | (2006.01) |
| C08J 3/20 | (2006.01) |
| C08L 53/00 | (2006.01) |
| C08L 33/12 | (2006.01) |

(52) U.S. Cl.
CPC ............ C08K 5/0008 (2013.01); A61L 9/014 (2013.01); C08J 3/203 (2013.01); C08L 53/00 (2013.01); C08J 2353/00 (2013.01); C08K 2201/007 (2013.01); C08L 33/12 (2013.01); C08L 2205/02 (2013.01)

(58) Field of Classification Search
CPC .................................................. C08K 5/0008
See application file for complete search history.

(56) References Cited

U.S. PATENT DOCUMENTS

| 4,102,807 A | 7/1978 | Iwama et al. |
| 5,849,310 A | 12/1998 | Trinh et al. |
| 7,708,982 B2 | 5/2010 | O'Leary et al. |
| 8,013,062 B2 | 9/2011 | Ruzette et al. |
| 8,461,098 B2 | 6/2013 | Guerret et al. |
| 9,296,854 B2 | 3/2016 | Bourrigaud et al. |
| 9,546,268 B2 | 1/2017 | Boutillier et al. |
| 2004/0253285 A1 | 12/2004 | O'Leary et al. |
| 2014/0030538 A1* | 1/2014 | Boutillier ................ C08L 53/00 428/520 |
| 2015/0177202 A1* | 6/2015 | Ozbek ................ G01N 33/0001 73/23.34 |

FOREIGN PATENT DOCUMENTS

| FR | 2916655 A1 | 12/2008 |
| JP | 51125442 A | 11/1976 |
| JP | 10316380 A | 12/1998 |
| JP | 2000506913 A | 6/2000 |
| JP | 2011527372 A | 10/2011 |
| WO | 9731623 A1 | 9/1997 |
| WO | 0040628 A1 | 7/2000 |
| WO | WO-0040628 A1 * | 7/2000 ............... A61K 8/90 |
| WO | 2013070564 A2 | 5/2003 |
| WO | 2003062293 A1 | 7/2003 |
| WO | 2004014438 A1 | 2/2004 |
| WO | 2008146119 A1 | 12/2008 |
| WO | 2010005690 A1 | 1/2010 |
| WO | 2010109582 A1 | 9/2010 |
| WO | 2012085487 A1 | 6/2012 |
| WO | 2012136941 A1 | 10/2012 |
| WO | 2013092958 A1 | 6/2013 |
| WO | 2015067722 A1 | 5/2015 |

OTHER PUBLICATIONS

International Search Report and Written Opinion for International Application No. PCT/EP2016/053581, dated Apr. 20, 2016—7 pages.
International Search Report and Written Opinion for International Application No. PCT/EP2014/073982, dated Jan. 21, 2015, 7 pages.
(National Pesticide Information Center, 2016, http://npic.orst.edu/envir/watersol.html), 3 pages.
Steinwall (Polymethy-methacrylate 2016; http://steinwall.com/wp-content/uploads/2016/05/Polymethyl-methacrylate-PMMA.pdf), 3 pages.
Polymerdatabase Properties (Crow 2015; http://polymerdatabase.com/polymer%20physics/Polymer%20Density.html), 3 pages.
Gent (Elastomer Chemical Compound, Britannica, Molecular Branching, 2017; http://www.britannica.com/science/elastomer), 9 pages.
Japanese Notice of Reasons for Refusal for Japanese Application No. 2017-542381, dated Dec. 16, 2019 with translation, 16 pages.

* cited by examiner

*Primary Examiner* — Michael F Pepitone
(74) *Attorney, Agent, or Firm* — RatnerPrestia

(57) ABSTRACT

The present invention relates to a composition comprising a polymeric elastomeric phase and an odoriferous active compound.
In particular the present invention relates to a composition comprising a polymeric elastomeric phase in form of an acrylic block copolymer and an odoriferous active compound, methods of absorption of odoriferous active compound and releasing said odoriferous active compound over a given period of time.
The present invention concerns also objects or articles comprising a polymeric elastomeric phase in form of an acrylic block copolymer and an odoriferous active compound, methods of absorption of odoriferous active compound by said objects and articles and releasing said odoriferous active compound over a given period of time.

19 Claims, No Drawings

US 10,808,099 B2

POLYMERIC COMPOSITION ABSORBING, COMPRISING AND RELEASING AN ODORIFEROUS ACTIVE COMPOUND, METHOD FOR PREPARING IT AND ITS USE

CROSS-REFERENCE TO RELATED APPLICATIONS

This patent application is a U.S. National Phase Patent Application of PCT Application No. PCT/EP2016/053581, filed Feb. 19, 2016, which claims priority to French Patent Application No. 15 51473, filed Feb. 20, 2015, each of which is incorporated by reference herein in its entirety for all purposes.

FIELD OF THE INVENTION

The present invention relates to a composition comprising a polymeric elastomeric phase and an odoriferous active compound.

In particular the present invention relates to a composition comprising a polymeric elastomeric phase in form of an acrylic block copolymer and an odoriferous active compound, methods of absorption of odoriferous active compound and releasing said odoriferous active compound over a given period of time.

The present invention concerns also objects or articles comprising a polymeric elastomeric phase in form of an acrylic block copolymer and an odoriferous active compound, methods of absorption of odoriferous active compound by said objects and articles and releasing said odoriferous active compound over a given period of time.

TECHNICAL PROBLEM

It is of great interest to have polymeric compositions or certain articles or objects made of polymeric compositions with a specific chosen odor. The odor of these polymeric compositions or certain articles shall not be only present at the beginning, but last a long time, in other words having a long lasting effect in terms of scenting. The characteristic chosen odor should be released over a given period of time.

Additionally, if the scent is getting less intense or is not present anymore it is difficult to renew it, especially if one does want to replace the complete object The objective of the present invention is to provide a polymeric composition with an odor and that the polymeric composition shall absorb easily and fast the odorant ingredient.

A further objective of the present invention is to provide a polymeric composition with an odor that can be scented for an extended length of time.

Another objective of the present invention is to provide a method to absorb easily and fast large quantities of the odorant ingredient.

Still a further object of the present invention is to provide a composition with the means of modulating the release of an odor.

Still another object of the present invention is to have a transformable polymeric composition with an odor or to produce an object comprising a polymeric composition with an odor.

Another objective of the present invention is an object that can release an odor that can be scented for an extended length of time.

Another objective of the present invention is to provide an article or object that can release an odor that can be "recharged" or reloaded when the odor or scent is less intense or lost.

Again still another objective of the present invention is altering the rate of evaporation of the specific odorant ingredient in a polymeric composition.

BACKGROUND OF THE INVENTION

The document WO2013/092958 describes core shell capsules comprising a polymeric shell and encapsulating a perfume containing oil core. The core shell capsule has to be ruptured in order to release the perfume.

The document WO2008/146119 describes a method for formulating odoriferous active ingredients in order to protect the same and to increase the persistence thereof. The method comprises the use of acrylic and thickening emulsions and especially the use of an hydrophobically alkali swellable emulsion.

The document WO 00/40628 discloses branched/block copolymers for treatment of keratinous substrates. The block copolymer consists of a hydrophilic block and a hydrophobic block. The block copolymer is soluble in water.

The document US2004/0253285 discloses gels for dispensing active volatile compounds. One component of the gel is a thermoplastic elastomer which is a polyether-ester-amide, which comprises semi-crystalline structures and blocks.

The document WO2013/070564 discloses a scent releasing articles and methods for producing the same. The scent releasing material comprises polymer material between opposing layers of a mesh material each, said polymer material is a thermoplastic or superabsorbent polymer.

The document WO2010/109582 discloses a porous hollow polymer particle which excels in extended release of fragrance material, light diffusion, liquid absorption, sensibility, solvent resistance and mechanical strength. Also disclosed are a fragrance material-carrying polymer particle which can stably carry fragrance material, while having excellent extended release of the fragrance material; a method for producing a porous hollow polymer particle; and a method for producing a fragrance material-carrying polymer particle.

In the prior art only polymeric particles, water soluble block copolymers or semi-crystalline elastomers are described, that contain a perfume or fragrance or an odoriferous active ingredient. There are no compositions comprising an elastomeric phase according to the invention.

Furthermore these polymer particles, microcapsule and water soluble copolymers are usually handled and formulated in aqueous phase and systems. The capsules are deposed on the surface of other materials. The capsules are sensible to mechanical stress. This make their use very limited, as they cannot be transformed or shaped into articles directly.

Especially there is no "recharge" or reload of the perfume or fragrance or an odoriferous active ingredient in the prior art.

BRIEF DESCRIPTION OF THE INVENTION

Surprisingly it has been discovered that an composition comprising an elastomeric phase of macromolecular sequences having a flexible nature with a glass transition temperature Tg of less than 20° C. formed from blocks of a block copolymer and at least one active ingredient as odoriferous active compound which is an organic molecule having a molecular weight of at least 16 g/mol and an odour threshold value in air of at least 0.5 ppb provides a polymeric composition with an odor and a fast absorption rate.

It has also been found that an composition comprising an elastomeric phase of macromolecular sequences having a flexible nature with a glass transition temperature Tg of less than 20° C. formed from blocks of a block copolymer and at least one active ingredient as odoriferous active compound which is an organic molecule having a molecular weight of at least 16 g/mol and an odour threshold value in air of at least 0.5 ppb provides polymeric composition with an odour that can be scented for an extended length of time and the composition can easily be reloaded with active ingredient.

DETAILED DESCRIPTION OF THE INVENTION

According to a first aspect, the present invention relates to a composition comprising
- an elastomeric phase of macromolecular sequences having a flexible nature with a glass transition temperature of less than 20° C. and
- at least one active ingredient as odoriferous active compound which is an organic molecule having a molecular weight of at least 16 g/mol and an odour threshold value in air of at least 0.5 ppb characterized that elastomeric phase of macromolecular sequences is formed from blocks of a block copolymer.

According to another aspect the present invention relates to an article made from a composition comprising
- an elastomeric phase of macromolecular sequences having a flexible nature with a glass transition temperature of less than 20° C. and
- at least one active ingredient as odoriferous active compound which is an organic molecule having a molecular weight of at least 16 g/mol and an odour threshold value in air of at least 0.5 ppb characterized that elastomeric phase of macromolecular sequences is formed from blocks of a block copolymer.

Still another aspect of the present invention is the use of a composition comprising
- an elastomeric phase of macromolecular sequences having a flexible nature with a glass transition temperature of less than 20° C. and
- at least one active ingredient as odoriferous active compound which is an organic molecule having a molecular weight of at least 16 g/mol and an odour threshold value in air of at least 0.5 ppb characterized that elastomeric phase of macromolecular sequences is formed from blocks of a block copolymer, for preparation of articles.

An additional aspect of the present invention is the method for preparation of a composition or an article comprising
- an elastomeric phase of macromolecular sequences having a flexible nature with a glass transition temperature of less than 20° C. and
- at least one active ingredient as odoriferous active compound which is an organic molecule having a molecular weight of at least 16 g/mol and an odour threshold value in air of at least 0.5 ppb characterized that elastomeric phase of macromolecular sequences is formed from blocks of a block copolymer.

By the term "polymeric elastomeric phase" as used is denoted the thermodynamic state of the polymer above its glass transition.

By the term "alkyl(meth)acrylate" as used is denoted to both species alkyl acrylate and alkyl methacrylate.

By the term "copolymer" as used is denoted that the polymers consists of at least two different monomers.

By the term "block copolymer" as used is denoted a copolymer composed of blocks, wherein the adjacent blocks are constitutionally different.

By the term "parts" as used herein is denoted "parts by weight".

By the term "thermoplastic polymer" as used is denoted a polymer that turns to a liquid or becomes more liquid or less viscous when heated and that can take on new shapes by the application of heat and pressure.

By the term "PMMA" as used are denoted homo- and copolymers of methyl methacrylate (MMA), for the copolymer of MMA the weight ratio of MMA inside the PMMA is at least 50 wt %.

Odoriferous active compounds are generally small molecular weight substances with a vapour pressure that allows their molecules to evaporate, become airborne, and eventually reach the olfactory organ of a living entity. There are a variety of different odoriferous active compounds with different functional groups and molecular weights, both of which affect their vapour pressures, and hence, the ease with which they can be sensed.

With regard to elastomeric phase of macromolecular sequences having a flexible nature, said macromolecular sequences have a glass transition temperature Tg of less than 20° C., preferably less than 10° C. and more preferably less than 0° C.

The elastomeric phase in the composition according to the invention can be a continuous phase, a semi-continuous or a discontinuous phase.

The macromolecular sequence with the flexible nature forming the elastomeric phase is part of a block copolymer with at least one block having a glass transition temperature Tg less than 20° C. preferably less than 10° C. and more preferably less than 0° C.

Preferably one of the at least other blocks is having a glass transition temperature Tg more than 20° C., preferably more than 30° C. and more preferably more than 40° C.

The block copolymer can be chosen from a thermoplastic block copolymer.

Advantageously the block copolymer is amorphous. More advantageously the block copolymer does not comprise any semi-crystalline or crystalline blocks.

Most preferably the thermoplastic block copolymer is a thermoplastic acrylic block copolymer. By this is meant that at least 30% wt %, preferably 40 wt % and more preferably 50 wt % of the monomers inside thermoplastic acrylic block copolymer are alkyl(meth)acrylate monomers.

Preferably the thermoplastic acrylic block copolymer is having a general formula $(A)_nB$ in which:
- n is an integer of greater than or equal to 1,
- A is: an acrylic or methacrylic or styrenic homo- or copolymer having a Tg of greater than 50° C., preferably of greater than 80° C., or polystyrene, or an acrylic/styrene or methacrylic/styrene copolymer;
- B is an acrylic or methacrylic or homo- or copolymer having a Tg of less than 20° C., Preferably, in the block A the monomer is chosen from methyl methacrylate (MMA), phenyl methacrylate, benzyl methacrylate, isobornyl methacrylate, styrene (Sty) or alpha-methylstyrene or mixtures thereof. More preferably, the block A is PMMA or PMMA copolymerized with acrylic or methacrylic comonomers or polystyrene (PS) or PS modified with styrenic comonomers.

Preferably the block B comprises monomers chosen of methyl acrylate, ethyl acrylate, butyl acrylate (BuA), ethylhexyl acrylate or butyl methacrylate and mixtures thereof, more preferably butyl acrylate said monomers make up at least 50 wt %, preferably 70 wt % of block B.

Furthermore, the blocks A and/or B can comprise other acrylic or methacrylic comonomers carrying various chemical function groups known to a person skilled in the art, for example acid, amide, amine, hydroxyl, epoxy or alkoxy functional groups. The block A can also incorporate groups, such as acrylic acid (AA) or methacrylic acid (MAA), in order to increase the thermal resistance of thereof.

Comonomers like styrene can also be incorporated in the block B in order to mismatch the refractive index of the block A.

Preferably, said thermoplastic acrylic block copolymer has a structure chosen from: ABA, AB, $A_3B$ and $A_4B$.

The thermoplastic acrylic block copolymer for example can be one of the following triblock copolymers: pMMA-pBuA-pMMA, p(MMAcoMAA)-pBuA-p(MMAcoMAA), pMMA-p(BuAcoSty)-pMMA, p(MMAcoMAA)-p(BuAcoSty)-p(MMAcoMAA) and pMMA-p(BuAcoAA)-pMMA. In a preferred embodiment, the block copolymer is of MMA type (PMMAcoMAA)-p(BuAcoSty)-P(MMAcoMAA).

It is also known to a person skilled in the art that the polymers of PMMA type can comprise small amounts of acrylate comonomer in order to improve the thermal stability thereof. By small is meant less than 9 wt %, preferably less than 7 wt % and more preferably less than 6 wt %.

The block B represents from 10 wt % to 85 wt % of the total weight of the block copolymer, preferably 25 wt % to 75 wt % and more preferably from 35 wt % to 65 wt %.

The block B has a weight-average molar mass of between 10 000 g/mol and 500 000 g/mol, preferably from 20 000 g/mol to 300 000 g/mol.

The block copolymers participating in the composition of the matrix can be obtained by controlled radical polymerization (CRP) or by anionic polymerization; the most suitable process according to the type of copolymer to be manufactured will be chosen.

Preferably, this will be CRP, in particular in the presence of nitroxides, for the block copolymers of $(A)_nB$ type and anionic or nitroxide radical polymerization, for the structures of ABA type, such as the triblock copolymer MAM.

With regard to the active ingredient or odoriferous active compound of the composition according to the invention is an organic molecule or a blend of organic molecules. The organic molecule is an odorant molecule.

The active ingredient can also be dissolved in a solvent which is not a good solvent of the block copolymer. The active ingredient can also be blended with at least another organic molecule, preferably not odoriferous in order to decrease the concentration of the odoriferous composition.

The organic molecule that is the odorant molecule and can be in one sense of the invention considered to be a material like a fragrance, perfume, aroma or flavour. However these are materials that are generally connected with a smell or scent that could be considered as pleasant. According to the invention the organic molecule that is the odorant molecule can also have an unpleasant smell like for example an organic amine compound or an organic thiol compound. The unpleasant smell can be used as a repulsing or repellant function. For example, the organic molecule can be geraniol which is known to be a very efficient anti-mosquito product.

The molecular weight M of the organic molecule that is the active ingredient is at least 16 g/mol, preferably at least 30 g/mol.

The odour threshold value in air of the organic molecule that is the active ingredient is at least 0.5 ppb.

Generally the organic molecule as active ingredient or odoriferous active has chemical groups as varied as alcohols, ketones, esters, ethers, acetates, alkenes, carboxylic acids, amines, lactones, aromatics, thio groups. The organic molecule can comprise only one or several of this chemical groups.

The organic molecule can for example be chosen from but is not limited to ethyl formate, ethyl acetoacetate, ethyl acetate, diethyl malonate, fructone, ethyl propionate, toluic aldehyde, leaf aldehyde, trans-2-hexenal, trans-2-hexenol, cis-3-hexenol, prenyl acetate, ethyl butyrate, hexanal, butyl acetate, 2-phenylpropanal, cis-4-heptenal, cis-3-hexenyl formate, propyl butyrate, amyl acetate, ethyl-2-methylbutyrate, ethyl amyl ketone, hexyl formate, 3-phenyl butanal, cis-3-hexenyl methyl carbonate, methyl phenyl carbinyl acetate, methyl hexyl ether, methyl cyclopentylidene acetate, 1-octen-3-ol, cis-3-hexenyl acetate, amyl vinyl carbinol, 2,4-dimethyl-3-cyclohexen-1-carbaldehyde, ethyl 2-methylpentanoate, 1,3,3-trimethyl-2-oxabicyclo[2.2.2]octane, 3,7-dimethyl-7-methoxyoctan-2-ol, methyl anthranylate, nerolidyl acetate, para-cresyl caprylate, para-cresyl, phenyl acetate, phenyl ethyl cinnamate, phenyl ethyl salicylate, tetradecariitrile, 2-methyl pyrazine, acetaldehyde phenylethyl propyl acetal, acetophenone, nonenylic aidhyde, allyl amyl glycolate, allyl caproate, amyl butyrate, aldehyde anisique, benzaldehyde, benzyl acetate, benzyl acetone, benzyl alcohol, benzyl butyrate, benzyl formate, benzyl isovalerate, benzyl methyl ether, berizyl propionate, butyl acetate, camphor, 3-methyl-5-propyl-2-cyclohexenone, cinnamic aldehyde, cis-3-hexenol, cis-3-hexenyl acetate, cis-3-hexenyl formate, cis-3-hexenyl iso-butyrate, cis-3-hexenyl propionate, cis-3-hexenyl tiglate, citronella!, citronellol, citronellyl nitrile, 2-hydroxy-3-methyl-2-cyclopenten-1-one, cuminic aldehyde, acetic acid (cycloheyloxy)-2-propenylester, damascenone, aipha-damascone, beta-daniascone, decahydro beta-napthyl formate, dietliyl inalonate, dihydrojasmone, dihydro-linalool, dihydro-myrcenol, dihydro-terpineol, dimethyl anthranilate, dimethyl benzyl carbinol, dimethyl benzy! carbinyl acetate, dimethyl octenone, dimyrcetol, estragole, ethy! acetate, ethyl aceto-acetate, ethyl benzoate, ethyl heptoate, ethyl linalool, ethyl salicylate, ethyl-2-methyl butyrate, eucalyptol, eugenol, fenchyl acetate, fenchyl alcohol, 4-phenyl-2,4,6-trimethyl 1,3-dioxane, methyl 2-octynoate, 4-isopropylcyclohexanol, 2-sec-butylcyclohexanone, styralyl acetate, geranyl nitrile, hexyl acetate, alpha-ionone, iso-amyl acetate, iso-butyl acetate, iso-cyclocitral, dihydroisoj asmone, iso-menthone, iso-pentyrate, iso-pulegol, cis-jasmone, laevo-carvone, phenylacetaldehyde glycerylacetal, carbinic acid 3-hexenyl methyl ether, 1-methyl-cyclohexa-I,3-diene, linalool, linalool oxide, 2-ethylethyl ester pentanoate, 2,6-dimethyl-5-heptenal, menthol, menthone, methyl acetophenone, methyl amyl ketone, methyl benzoate, alpha-methyl cinnamic aldehyde, methyl heptenone, methyl hexyl ketone, methyl para cresol, methyl phenyl acetate, methyl salicylate, 4-tert-pentyl-cyclohexanone, para-creso, para-cresyl acetate, para-t-butylcyclohexanone, para-toluyl aldehyde, phenyl acetaldehyde, phenyl ethyl acetate, phenyl ethyl alcohol, phenyl ethyl butyrate, phenyl ethyl formate, phenyl ethyl iso butyrate, pheny ethyl propionate, phenyl propyl acetate, pheny! propyl aldehyde, tetrahydro-2,4-dimethyl-4-pentyl-furan, 4-methyl-2-(2-methyl-1-propenyl)tetrahydropyran, 5-Methyl-3-heptanone oxime, styralyl propionate, styrene, 4-methylphenylacetaldehyde, terpineol, terpinolene, tetrahydro-linalool, tetrahydro-rnyrcenol, trans-2-hexenal, verdyl acetate, vanillin, or mixtures thereof.

The organic molecule that is the active ingredient is not an organic molecule coming from the other components of the composition. By this is meant that it is not a residual monomer introduced in the composition with the thermoplastic polymer or for example with the block copolymer for the elastomeric domains. If the thermoplastic polymer is for example polystyrene, the residual styrene monomer is not considered as active ingredient according to the invention. If the elastomeric domains comprises for example polybutylacrylate blocks, the residual butyl acrylate monomer is not considered as active ingredient according to the invention.

The composition according to the invention comprises at least 1 ppm of the organic molecule as active ingredient or odoriferous active compound relative by weight to the block copolymer, preferably at least 10 ppm and more preferably at least 100 ppm, even more preferably 1 000 ppm, advantageously 10 000 ppm, more advantageously at least 10 parts relative by weight to 100 parts of the block copolymer and most advantageously more than 11.5 parts relative by weight to 100 parts of the block copolymer.

The polymeric composition according to the invention comprises between $1*10^{-6}$ parts and 300 parts by weight of the organic molecule as active ingredient or odoriferous active compound relative by weight to 100 parts of the block copolymer, preferably between $1*10^{-4}$ parts and 300 parts by weight and more preferably between 1 part and 300 parts by weight, still more preferably between 11.5 parts and 300 parts by weight.

The composition comprising the elastomeric phase according to the invention can absorb more than 10 ppm by weight of the organic molecule as active ingredient or odoriferous active compound, preferably more than 100 ppm, more preferably more than 1000 ppm, advantageously more than 1 wt %, more advantageously more than 5 wt % and even more advantageously more than 10 wt % relative to the block copolymer. The absorption time for 50 wt % of the organic molecule as active ingredient or odoriferous active compound is less than 4 hours, preferably less than 3 hours.

The composition comprising the elastomeric phase according to the invention can absorb between $1*10^{-6}$ parts and 300 parts by weight of the organic molecule as active ingredient or odoriferous active compound relative by weight to 100 parts of the block copolymer, preferably between $1*10^{-4}$ parts and 300 parts by weight and more preferably between 1 part and 300 parts by weight, still more preferably between 11.5 parts and 300 parts by weight.

The elastomeric phase of the composition makes up at least 1 wt %, preferably at least 2 wt %, more preferably at least 3 wt %, advantageously at least 5 wt %, more advantageously at least 7 wt % and most advantageously at least 10 wt %.

According to a further aspect the composition according to the invention can comprise a further polymer P.

According to one embodiment the composition of the present invention can comprise also at least one additional polymer P, said polymer P makes up less than 80 wt % of the composition.

According to another embodiment the composition of the present invention can be comprised in at least one polymer P, said polymer P makes up at least 80 wt % of the composition.

The polymer P can be added in order to make it odoriferous thanks to the presence of elastomeric phase of macromolecular sequences having a flexible nature with a glass transition temperature of less than 20° C. of the block copolymer and the at least one active compound in the whole composition. In that case of the block copolymer, the polymer P is preferably compatible with at least one block of the block copolymer.

With regard to the polymer P, it is preferably a thermoplastic polymer or a crosslinked polymer comprising thermoplastic polymer chains between the cross linking points.

In one embodiment the polymer P is a crosslinked polymer, and it is preferably cross-linked acrylic polymer particles as described in the document EP2694583. When these particles are added in the composition, their ratio is from 2% to 50% and more preferably from 5% to 30% in weight of the block copolymer.

In another embodiment the polymer P is a thermoplastic polymer.

The thermoplastic polymer is chosen from poly(vinyl chloride) (PVC), polyesters as for example poly (ethylene terephthalate) (PET) or poly(butylene terephthalate) (PBT) or polylactic acid (PLA), polystyrene (PS), polycarbonates (PC), polyethylene, poly (methyl methacrylate)s, (meth) acrylic copolymers, thermoplastic poly(methyl methacrylate-co-ethylacrylates), poly(alkylene-terephthalates), poly vinylidene fluoride, poly(vinylidenchloride), polyoxymethylen (POM), semi-crystalline polyamides, amorphous polyamides, semi-crystalline copolyamides, amorphous copolyamides, polyetheramides, polyesteramides, copolymers of styrene and acrylonitrile (SAN), and their respective mixtures.

The polymeric polymer P can also be a blend of several thermoplastic polymers.

Preferably the thermoplastic polymer is a methacrylic polymer.

Preferably the thermoplastic polymer is a methacrylic polymer comprising at least 50 wt % methyl methacrylate.

In still another embodiment the polymer P is a mixture of a thermoplastic polymer and a crosslinked polymer comprising thermoplastic polymer chains between the cross linking points.

The thermoplastic polymer and the crosslinked polymer are the same as defined for the other embodiments.

The method for preparation of a composition or an article according to the invention comprises the step of bringing into direct contact the elastomeric phase of macromolecular sequences having a flexible nature with a glass transition temperature of less than 20° C. in form of a block copolymer and the least one active ingredient as odoriferous active compound which is an organic molecule having a molecular weight of at least 16 g/mol and an odour threshold value in air of at least 0.5 ppb.

The direct contact of the compounds for the method of preparation of composition or article can be made by several methods.

A first method of preparation of a composition according to the invention comprises a blending step of the respective compounds.

A method of preparation of the composition according to the invention is blending a component comprising the elastomeric phase of macromolecular sequences having a flexible nature with the active ingredient as odoriferous active compound.

The two components could be heated if necessary during blending

Mixing could also be obtained by dry blending a solid resin comprising the elastomeric phase of macromolecular sequences having a flexible nature and solid active ingredient as odoriferous active compound.

A second method of preparation of a composition according to the invention comprises the step of absorption of at least one active ingredient as odoriferous active compound by the macromolecular sequences having a flexible nature. Therefore the odoriferous active compound is either liquid or dissolved in a solvent which is not a good solvent of the block copolymer. The active ingredient can also be blended with at least another organic molecule, preferably not odoriferous, in order to decrease the concentration of the odoriferous composition.

The elastomeric phase of macromolecular sequences having a flexible nature with a glass transition temperature of less than 20° C. or a composition comprising it is dipped or immersed in the liquid or solution. The quantity of the absorbed liquid or solution is in relation with the duration time of the dipping or immersion.

A third method of preparation of a composition according to the invention comprises the step of transferring to the surface of the elastomeric phase of macromolecular sequences having a flexible nature with a glass transition temperature of less than 20° C. or a composition comprising it the active ingredient or a solution comprising the active ingredient. This can be for example the composition transformed to a sheet and the surface of that sheet is treated with the liquid active ingredient or a solution comprising of the active ingredient by means of a brush. The liquid active ingredient or a solution comprising of the active ingredient is absorbed by the composition. The application with the brush can be repeated several times.

The absorption corresponding to the second and third method is very quick, and quicker than with other polymers used in this type of application as polyether-block-amide copolymer or an ethylene-vinylacetate copolymer.

The second and third method have the advantage that a possible loss of the active ingredient as odoriferous active compound is reduced.

The composition according to the invention prepared by the second or third method can absorb and comprise up to 300 parts by weight of the organic molecule as active ingredient or odoriferous active compound relative to 100 parts of the block copolymer comprising the elastomeric phase of macromolecular sequences.

The composition according to the invention prepared by the second or third method comprises between $1*10^{-6}$ parts and 300 parts by weight of the organic molecule as active ingredient or odoriferous active compound relative by weight to 100 parts of the block copolymer, preferably between $1*10^{-4}$ parts and 300 parts by weight and more preferably between 1 part and 300 parts by weight, still more preferably between 11.5 parts and 300 parts by weight.

The composition according to the invention can be transformed by injection molding, extrusion, coextrusion or extrusion/blow molding for the preparation of parts, profiled elements, sheets or films, for example, or for producing an article.

In one embodiment the composition of the invention can comprise additionally fillers. The active ingredient or odoriferous active compound of the composition is connected to the nature of the filler. The odour of the active ingredient or odoriferous active compound is directly linked to the macroscopic appearance of the filler in its natural state. The active ingredient or odoriferous active compound has an odour that is close or identical to the appearance of the filler.

The filler in its natural state has a characteristic odour. The filler is for example chosen from wood, cork or other natural organic material. The active ingredient or odoriferous active compound possesses the odour linked to the nature of the filler added. When the filler for example is based on wood or wood like components, the active ingredient or odoriferous active compound has the scent or odour of wood. When the filler for example is based on cork or cork like components, the active ingredient or odoriferous active compound has the scent or odour of cork. When the filler for example is based on the colour of a certain fruit or flower, the active ingredient or odoriferous active compound has the scent or odour of the respective fruit or flower. The same concept applies for other kind of fillers.

The composition of the invention can be used for making an article or be used to be part of an article.

The composition of the invention can be transformed into an article or be part of an article.

The articles of the invention can for example be in form of a sheet, block, film, tube or profiled element. The articles can be at least partly foamed.

The articles of the invention can also be prepared by first manufacturing an article which is transformed to an article according to the invention by using the second and third method described earlier. Therefore an a polymeric composition comprising an elastomeric phase of macromolecular sequences having a flexible nature with a glass transition temperature of less than 20° C. is transformed by injection molding, extrusion, coextrusion or extrusion/blow molding for the preparation of parts, profiled elements, sheets or films, for example, or for producing an article which can be further proceeding by using second or third method of preparation of a composition according to the invention.

The articles according to the invention can be transparent including a non transparent object.

The articles according to the invention can have a glossy or matt surface.

Examples for articles are decking or siding parts, window profiles, baseboard, furniture articles, glazing, displays, lighting objects that can be rigid or flexible, mobile telephone protection case, smartphone protection case, tablet computer protection case or laptop, bracelets or bracelets for wrist watches, rings or jewelry parts, part of floor coatings, artificial wood, urinal parts.

[Methods]

The weight average molecular weight of polymeric compound can be measure by size exclusion chromatography (SEC).

The glass transition temperature (Tg) of the polymers are measured with equipment able to realize a thermo mechanical analysis. A RDAII "RHEOMETRICS DYNAMIC ANALYSER" proposed by the Rheometrics Company has been used. The thermo mechanical analysis measures precisely the visco-elastics changes of a sample in function of the temperature, the strain or the deformation applied. The apparatus records continuously, the sample deformation, keeping the stain fixed, during a controlled program of temperature variation.

The results are obtained by drawing, in function of the temperature, the elastic modulus (G'), the loss modulus and the tan delta. The Tg is higher temperature value read in the tan delta curve, when the derived of tan delta is equal to zero.

EXAMPLES

The series of examples concern the preparation of and absorption and desorption of an active ingredient (odoriferous active compound) by different polymeric compounds or compositions some of them comprising elastomeric domains coming from block copolymers.

Examples General Procedure Absorption

An absorption kinetic of a fragrance named "bois de chêne" commercialized under the reference EAD000956/00 by the company GIVAUDAN is established with different polymers.

3 g of each polymer $P_n$ is put in a metallic basket 40 mm lateral length, made of perforated metal sheet with wholes of 1.5 mm. The mass of the two together is measured with a balance. The basket is then completely immersed in a beaker filled with the liquid fragrance, stirred with a magnetic stirrer. The temperature is between 20° C. and 25° C. After 1 minute of complete immersion the basket is retrieved and put three times for ten seconds on a clean absorbing paper. The complete mass is measured, the difference would make up the quantity of the absorbed fragrance. After weighting the basket is immediately put back in into the fragrance solution. Until 120 minutes the every 15 minutes the mass is controlled based on the procedure described above and following this every 30 minutes until 8 hours. After 24 hours a last weighting is performed in order to estimate a kind of approach to a maximal absorption of the polymer. This allows to follow the absorption of the fragrance by the respective polymers Pn as function of the immersion time.

Following polymers $P_n$ are tested:

Example 1

Polymer P1 is a composition composed of:
18% of crosslinked acrylic particles made of PMMA-PS copolymer. The copolymer contains 25% of styrene. The weight average size of the crosslinked particles is 50 μm
10% of an acrylic copolymer composed by 60% of MMA and 40% of butyl methacrylate (BMA). The molecular weight of the copolymer is Mw=45000 g/mol.
and 72% of Polymer P2 (see example 2).
P1 contains 36% of soft phase.

Example 2

Polymer P2 is a triblock PMMA-PBuA-PMMA copolymer containing 50% in weight of PBuA. The Mw of the PbuA block is 50 000 g/mol. The polymer P2 contains 50 wt % of soft phase

Comparative Example 3

Polymer P3 is a Polyether-block-amide copolymer commercialized by Arkema under the reference PEBAX 2533 SA01. The polymer P3 contains 25 wt % of soft phase. Comparative example 4: polymer P4 is a vinyl acetate-ethylene copolymer commercialized by Arkema under the reference EVATANE 2825.

Comparative Example 5

Polymer P5 is a Butylacrylate-ethylene copolymer commercialized by Arkema under the reference Lotryl 30BA02.
The absorption time for same quantity of fragrance is compared for all polymers.

TABLE 1 comparison of absorption

| | Polymer | Time to reach 17.6 parts of fragrance absorbed in 100 parts of polymer P [min] | Time to reach 43 parts of fragrance absorbed in 100 parts of polymer P [min] |
|---|---|---|---|
| Example 1 | P1 | 25 | 86 |
| Example 2 | P2 | 15 | 46 |
| Comparative example 3 | P3 | 52 | 180 |
| Comparative example 4 | P4 | 90 | 375 |
| Comparative example 5 | P5 | 300 | >24 h |

The polymers P1 and P2 allow the shortest absorption time for the same quantity of fragrance. The polymer P1 and P2 absorb more fragrance than other polymers during the first hours of impregnation.

Examples General Procedure Desorption

A desorption kinetic of a fragrance named "bois de chêne" commercialized under the reference EAD000656/00 by the company GIVAUDAN is established with different polymers. The quantity of the fragrance is 30 wt %. In a closed glass flask 7 g of polymer Pn are brought together with 3 g of the fragrance. The two components are mixed for 24 hours. The fragrance has been completely absorbed by the polymer after that time. Each sample is put in a tared open recipient and the loss of weight is measured at 2 hours, 3 hours, 7 hours and then every 24 hours (except on weekends)

The kinetic of the weight loss are followed for the same polymers P1 to P4 as before.

TABLE 2 comparison of loss of fragrance

| | | Loss after number of days/[%] days | | | | | |
|---|---|---|---|---|---|---|---|
| | Polymer | 1 | 3 | 6 | 10 | 15 | 20 |
| Example 1 | P1 | 3.0 | 6.0 | 10.0 | 14.3 | 21.3 | 21.3 |
| Example 2 | P2 | 3.7 | 7.0 | 10.7 | 16.7 | 22.7 | 24.7 |
| Comparative example 3 | P3 | 3.7 | 6.7 | 10.0 | 15.0 | 21.3 | 21.0 |
| Comparative example 4 | P4 | 3.7 | 7.0 | 9.7 | 17.7 | 23.3 | 22.3 |

The polymers P1 and P2 of the polymer composition according to the invention has the same kinetic of desorption as the other comparative polymers.

Example Absorption of an Article

A film of 300 μm thickness is extruded with polymer P1 at 200° C. in an extruder from the company Andouart.

At 20° C. the fragrance named "bois de chêne" commercialized under the reference EAD000656/00 by the company GIVAUDAN is applied with a brush on the surface of the film. After a few minutes the liquid fragrance is not visible anymore at the surface of the film, the film seems dry when touching it. The film possesses the characteristic odor of the fragrance.

When the intensity of the odor decreases and is not sufficient anymore or if the odor has to be changed to another one, the application procedure can be remade, and avoids to manufacture again this film or any other article or object.

The invention claimed is:

1. A composition comprising:
an elastomeric phase of macromolecular sequences having a flexible nature with a glass transition temperature of less than 20° C.; and
at least one active ingredient as odoriferous active compound which is an organic molecule having a molecular weight of at least 16 g/mol and an odor threshold value in air of at least 0.5 ppb;
wherein
the elastomeric phase of macromolecular sequences is formed from blocks of a block copolymer; and
the block copolymer comprises at least one triblock copolymer selected from the group consisting of pMMA-pBuA-pMMA, p(MMAcoMAA)-pBuA-p(MMAcoMAA), pMMA-p(BuAcoSty)-pMMA, p(MMAcoMAA)-p(BuAcoSty)-p(MMAcoMAA) and pMMA-p(BuAcoAA)-pMMA.

2. The composition according to claim 1, wherein the composition comprises at least 1 ppm of the organic molecule as active ingredient or odoriferous active compound relative by weight to the block copolymer.

3. The composition according to claim 1, wherein the composition comprises more than 11.5 parts relative by weight of active ingredient to 100 parts of the block copolymer.

4. The composition according to claim 1, wherein the quantity of active ingredient is between 11.5 parts and 300 parts by weight relative to 100 parts of the block copolymer.

5. The composition according to claim 1, wherein the elastomeric phase of the composition makes up at least 1 weight %.

6. The composition according to claim 1, wherein it comprises a further polymer P.

7. The composition according to claim 6, wherein said further polymer P is a thermoplastic polymer.

8. The composition according to claim 6, wherein said further polymer P is a crosslinked polymer.

9. The composition according to claim 6, wherein said further polymer P is a mixture of a thermoplastic polymer and a crosslinked polymer comprising thermoplastic polymer chains between the cross linking points.

10. The composition according to claim 1, wherein the composition comprises additionally a filler.

11. The composition according to claim 10, wherein the active ingredient has an odor linked to the macroscopic appearance of the filler in its natural state.

12. A method for preparing a composition according to claim 1 comprising the step of bringing into direct contact the elastomeric phase of macromolecular sequences having a flexible nature with a glass transition temperature of less than 20° C. in form of a block copolymer and the least one active ingredient as odoriferous active compound which is an organic molecule having a molecular weight of at least 16 g/mol and an odor threshold value in air of at least 0.5 ppb.

13. The method according to claim 12, comprising the step of blending of the respective compounds.

14. The method according to claim 12, comprising the step of absorption of at least one active ingredient as odoriferous active compound by the macromolecular sequences having a flexible nature.

15. The method according to claim 14, wherein the absorption is done by dipping or immersing the block copolymer in liquid of the active ingredient or solution comprising the active ingredient.

16. The method according to claim 14, wherein the absorption is done by transferring to the surface of the composition comprising the block copolymer or an article comprising the block copolymer a liquid of the active ingredient or solution comprising the active ingredient.

17. An article comprising a composition according to claim 1.

18. The article according to claim 17, wherein the article is in the form of a sheet, block, film, tube, or profiled element.

19. The article according to claim 17, wherein the article is selected from the group consisting of decking parts, siding parts, window profiles, baseboards, furniture articles, glazing, displays, lighting objects that can be rigid, lighting articles that can be flexible, mobile telephone protection cases, smartphone protection cases, tablet computer protection cases, laptops, bracelets, bracelets for wrist watches, rings, jewelry parts, part of floor coatings, artificial wood, and urinal parts.

* * * * *